(12) United States Patent
Brock-Fisher (10) Patent No.: US 7,625,341 B2
(45) Date of Patent: *Dec. 1, 2009

(54) ELEVATION BEAMWIDTH CONTROL FOR CONTRAST IMAGING

(75) Inventor: George A Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 562 days.

This patent is subject to a terminal disclaimer.

(21) Appl. No.: 11/073,104

(22) Filed: Mar. 4, 2005

(65) Prior Publication Data

US 2005/0203408 A1   Sep. 15, 2005

Related U.S. Application Data

(63) Continuation of application No. 10/291,010, filed on Nov. 8, 2002.

(51) Int. Cl.
*A61B 8/00* (2006.01)

(52) U.S. Cl. ........................ 600/447; 600/458

(58) Field of Classification Search ................. 600/437, 600/440, 441, 443, 447, 453, 458, 504–507; 424/9.5–9.52
See application file for complete search history.

(56) References Cited

U.S. PATENT DOCUMENTS

| | | | | |
|---|---|---|---|---|
| 5,628,322 A * | 5/1997 | Mine | ........................... | 600/453 |
| 5,732,707 A * | 3/1998 | Widder et al. | ................ | 600/458 |
| 5,738,098 A * | 4/1998 | Brock-Fisher et al. | ....... | 600/472 |
| 5,833,613 A * | 11/1998 | Averkiou et al. | ............ | 600/440 |
| 5,833,615 A * | 11/1998 | Wu et al. | ..................... | 600/458 |
| 5,860,931 A * | 1/1999 | Chandler | ..................... | 600/458 |
| 5,911,221 A * | 6/1999 | Teo | .............................. | 600/447 |
| 5,944,666 A * | 8/1999 | Hossack et al. | ............. | 600/458 |
| 5,947,904 A * | 9/1999 | Hossack et al. | ............. | 600/458 |
| 6,004,270 A * | 12/1999 | Urbano et al. | .............. | 600/443 |
| 6,015,384 A * | 1/2000 | Ramamurthy et al. | ....... | 600/440 |
| 6,080,107 A * | 6/2000 | Poland | ........................ | 600/458 |
| 6,080,386 A * | 6/2000 | Porter | ........................ | 424/9.52 |
| 6,086,540 A * | 7/2000 | Bonneville et al. | .......... | 600/458 |
| 6,245,019 B1 * | 6/2001 | Kamiyama | ................... | 600/458 |
| 6,340,348 B1 * | 1/2002 | Krishnan et al. | ............ | 600/447 |
| 6,468,216 B1 * | 10/2002 | Powers et al. | ............... | 600/443 |
| 6,491,633 B1 * | 12/2002 | Krishnan et al. | ............ | 600/447 |
| 6,524,247 B2 * | 2/2003 | Zhao et al. | ................... | 600/437 |
| 6,692,438 B2 * | 2/2004 | Skyba et al. | ................. | 600/440 |
| 6,733,453 B2 * | 5/2004 | Freiburger et al. | .......... | 600/447 |
| 6,884,407 B1 * | 4/2005 | Unger | ........................ | 424/9.52 |
| 2001/0056236 A1 * | 12/2001 | Angelsen | ..................... | 600/458 |
| 2003/0114759 A1 * | 6/2003 | Skyba et al. | ................. | 600/458 |
| 2004/0138567 A1 * | 7/2004 | Ito et al. | ..................... | 600/458 |
| 2004/0228800 A1 * | 11/2004 | Alt | ............................. | 424/9.52 |

\* cited by examiner

*Primary Examiner*—Long V Le
*Assistant Examiner*—Salieu M Abraham (57) ABSTRACT

The present disclosure relates to contrast imaging. More particularly, the present disclosure relates to apparatus and methods for contrast imaging in which the elevation beamwidth is controlled to reduce image artifacts, which result from contrast agent being carried into the image region by motion or respiration and not by reperfusion.

1 Claim, 8 Drawing Sheets

ELEVATION BEAMWIDTH CONTROL FOR CONTRAST IMAGING

CROSS REFERENCE TO RELATED APPLICATION

This is a continuation of prior application Ser. No. 10/291,010, filed 8 Nov. 2002.

BACKGROUND OF THE INVENTION

1. Field of the Invention

The present disclosure relates to contrast imaging. More particularly, the present disclosure relates to apparatus and methods for contrast imaging in an ultrasound device in which elevation beamwidth is controlled to reduce image artifacts, which result from a contrast agent being carried into the image region by motion or respiration and not by reperfusion.

2. Description of the Related Art

Ultrasound imaging is widely used for medical imaging due to its safety, good image quality, and low cost and includes both tissue imaging and contrast imaging. Contrast imaging involves the use of intravenous contrast agents, which are encapsulated micro-bubbles, which are prepared and injected intravenously into the venous return system of the body of a patient. In particular, micro-bubbles are bubbles in the range of less than about 15 microns in diameter and include a heavy gas or air encapsulated with some form of shell, which can be, for example human albumin, a lipid protein, or a sugar. Micro-bubbles have characteristics that make them useful in contrast imaging both as tracers to show blood flow to or through the imaged tissue and also to quantify the rate of blood flow to or through the imaged tissue. The contrast agents can be easily detected and imaged because they resonate in the presence of ultrasonic fields producing radial oscillations. This resonant behavior gives rise to a non-linear acoustic response, typically a second harmonic response; but there are also other non-linear responses that can be detected.

A second characteristic of micro-bubbles, which is also useful, is that if excited with a large enough acoustic pressure in the range of contemporary ultrasound systems, the micro-bubbles can be destroyed by disrupting their shells and thereby allowing the encapsulated gas to escape. The gas from the destroyed micro-bubbles then dissolves into the blood stream.

Several techniques have been developed which take advantage of the primarily linear response behavior of tissue to cancel or attenuate tissue signals when ultrasound imaging is applied to the body of a patient, thereby providing an improved image of the contrast agents. In several of these techniques, multiple transmit lines are fired along the same line of sight into the body of the patient. The transmit waveform is modified (e.g., in terms of power, phase, or polarity) from line to line to produce a variation in the response received by the ultrasound transducer. These data points are then processed to remove the influence of their linear components, which are primarily related to the tissue signal, to yield data that primarily contains the non-linear response of the contrast agents.

Regardless of the technique used to image contrast agent, it is desirable to determine the rate of flow (perfusion) of blood in myocardial tissue. Because the flow rates are low, a general technique has been employed to measure the rate of reperfusion as follows. The contrast agent is administered to the patient, after which the contrast agent enters the right side of the heart and myocardial tissue. The contrast agent is first imaged and then is destroyed by high intensity ultrasound signals, thereby creating a 'negative bolus' effect. After the contrast agent is destroyed, the area of interest is subsequently scanned (imaged) and the intensity due to contrast agent is observed as it increases, indicating reperfusion within the scanned tissues.

Although the above-mentioned techniques work well in removing the influence of the tissue signal, artifacts from the contrast agent, which does not have a primarily linear response behavior, moving into the image plane caused by motion can degrade the resultant images. In particular, to obtain an accurate estimate of the rate of blood flow, only reperfusing contrast agent reperfusion, which corresponds with the rate of blood flow, should be imaged. The above-mentioned techniques are used to cancel or attenuate the linear signals of the tissue, and can include cancellation or attenuation of linear signals from tissue, which moves by either patient motion or respiration into the image area. These techniques, however, do not effectively compensate for the effect of the micro-bubbles in the moving tissue because the micro-bubbles produce this primarily non-linear response. Contrast agent, lying outside of the area, which was depleted of the contrast agent by high intensity ultrasound, can be carried by motion into the imaging plane. The contrast agent movement into the image plane can cause degraded images that cannot be effectively compensated for with typical processing techniques. This degradation can be substantial, particularly where the heart or lungs is being imaged due to their frequent and rapid motions.

What is needed is an apparatus and method for contrast imaging in which the response of a contrast agent from the area surrounding the image plane, which moves into the image plane, is effectively suppressed so as to enhance the imaging of only reperfused contrast agent, thereby increasing the accuracy of the imaging of the rate of the blood flow to or through the tissue in the image plane.

SUMMARY OF THE INVENTION

The present disclosure relates to apparatus and methods for imaging contrast agents within a patient's body. The method generally comprises configuring a ultrasound system to transmit a high intensity ultrasound beam having a thick elevation focus; transmitting the high intensity ultrasound beam; waiting a predetermined delay time; configuring the ultrasound system to have a thinned elevation focus; transmitting a lower intensity ultrasound beam; receiving the echoed image from the image plane of the reperfused contrast agent which represents the rate of the blood flow; and producing an image for the user to view.

In an embodiment, the process is iteratively repeated with different predetermined delay times to produce an accurate determination of rate of blood flow in the tissue within the image plane. The reperfusion of the contrast agent over time is a function of blood volume flow and by delaying imaging at the image plane by different predetermined delay times reperfusion of the contrast agent can be measured and an accurate rate of the blood flow can be determined.

An aspect of the present invention is to provide an ultrasound imaging system for contrast imaging, which uses a contrast agent, and is able to preferentially detect substantially only a reperfused contrast agent and substantially eliminate echoes due to contrast agent movement into the image plane so that an improved visualization of the reperfused contrast agent, which represents blood flow is realized.

Another aspect of the present invention is to provide an ultrasound imaging system for contrast imaging, in which the transmitted ultrasound beams can be focused to produce a destructive region of the contrast agent, which is the region of the contrast agent destroyed during the transmission of high intensity ultrasound beam, and which region has a thickness greater than the imaging plane thickness.

An additional aspect of the present invention is to provide a method for ultrasound contrast imaging, in which the transmitted and received ultrasound beams are focused, producing a destructive thickness of the contrast agent, which is greater than the imaging plane thickness.

A further aspect of the present invention is to use a two dimensional array of transducer elements for ultrasound contrast imaging to electrically steer and focus the transmitted and received ultrasound beams producing an improved visualization of the reperfused contrast agent.

Another aspect of the present invention is to control the elevation beamwidth used in contrast imaging by changing the frequency of the transmitted and received ultrasound beams.

An aspect of the present invention is to control the elevation beamwidth used in contrast imaging by changing the effective elevation aperture of the transmitted and received ultrasound beams.

A further aspect of the present invention is to control the elevation beamwidth used in contrast imaging by selectively using the central elements of the widely spaced elements of an ultrasound transducer to change the focal depth.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION OF THE PREFERRED EMBODIMENTS

The features and advantages of the invention will become apparent upon reading the following specification, when taken in conjunction with the accompanying drawings.

The present disclosure generally relates to contrast imaging. According to one aspect of the invention, contrast agent detection techniques are used to image a contrast agent in image planes of the body of a patient. In another aspect of the invention, these techniques are used to measure the concentration of the contrast agent over predetermined intervals to establish the velocity of contrast agent flow through the bloodstream. In either case, in contrast imaging of moving tissue, for example in heart or lung imaging, by destroying the contrast agent in the area surrounding the image plane, the effect of the contrast agent in the surrounding tissue moving into the image plane can be substantially eliminated, thereby producing a contrast image which corresponds substantially to reperfusion of the contrast agent and, in particular, not the movement of the contrast agent in the surrounding tissue. Reperfusion of the contrast agent can be more clearly imaged and accurate estimates of the direction and of the velocity of the contrast agent flow through the bloodstream can be established.

Figure 1:
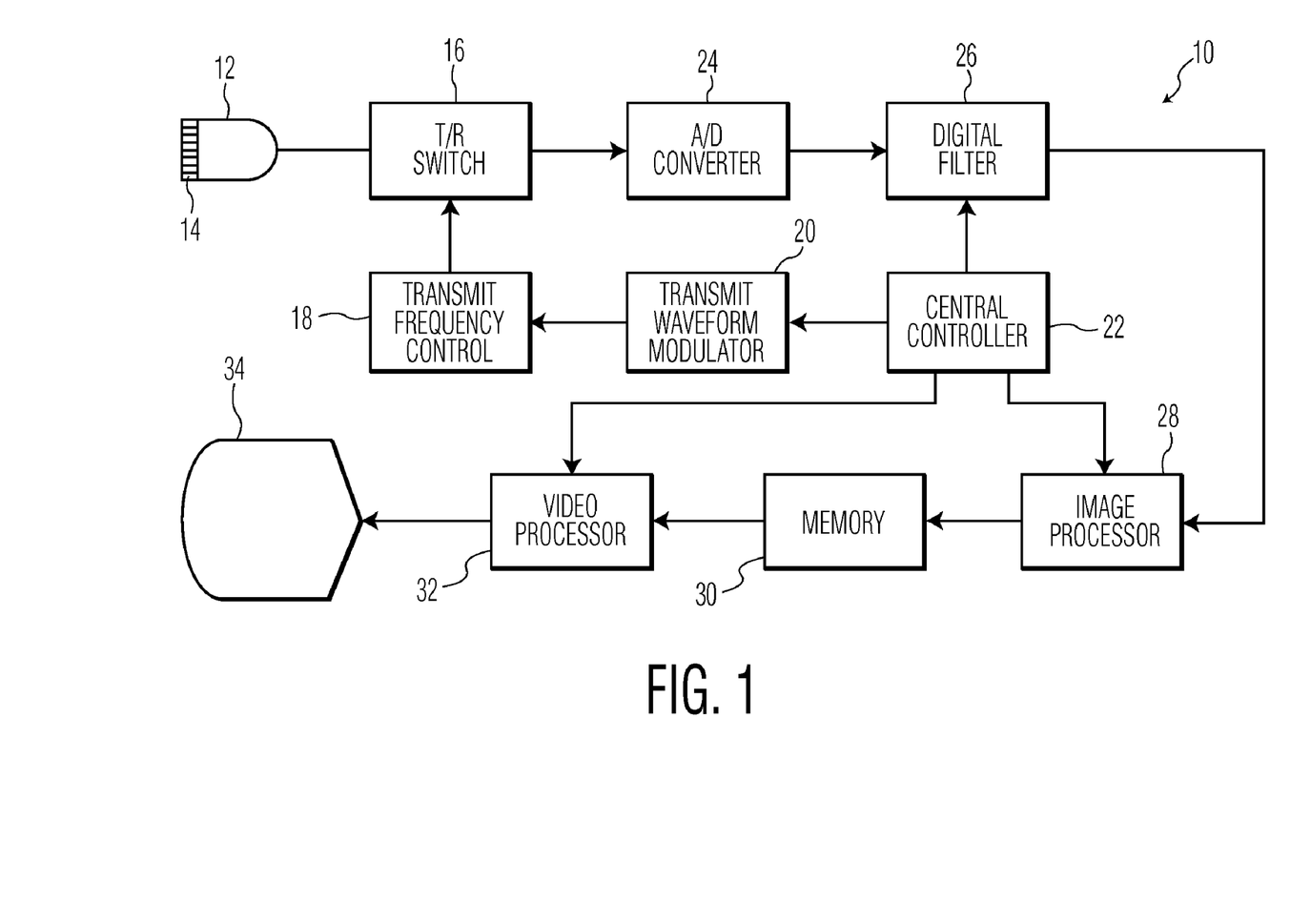
FIG. 1 is a block diagram of a contrast imaging system of the present invention.

Referring now in more detail to the drawings, in which like numerals indicate corresponding parts throughout the several views, FIG. 1 illustrates a contrast imaging system 10 of the present invention. It will be appreciated that this figure does not necessarily illustrate every component of the system, emphasis instead being placed upon the components most relevant to the methods disclosed herein. As indicated in FIG. 1, the system 10 comprises a probe 12 that includes a transducer array of matrix elements 14, preferably a two-dimensional matrix array of elements 14 that is used to transmit and receive signals. The probe 12 is electrically connected to a T/R switch 16 which places the probe in a transmit mode or a receive mode. On the transmit side, the system 10 includes a transmit frequency control 18 and a transmit waveform modulator 20 that, under the control of a central controller 22, sets the transmit frequency of the transmit signals and modulates the various transmitted signal lines, respectively.

On the receive side, the system 10 includes an A/D converter 24 which converts the analog signals received from the probe 12 into digital signals and a digital filter 26 (e.g., an RF filter) that filters signals outside the desired receive band from the received data. In addition, the receive side includes an image processor 28 which can record the data for tissue motion effects and can, for instance, suppress the stationary tissue signal components. The corrected data can be stored in a memory 30 and, after being processed by a video processor 32, displayed on a display device 34.

Figure 2:
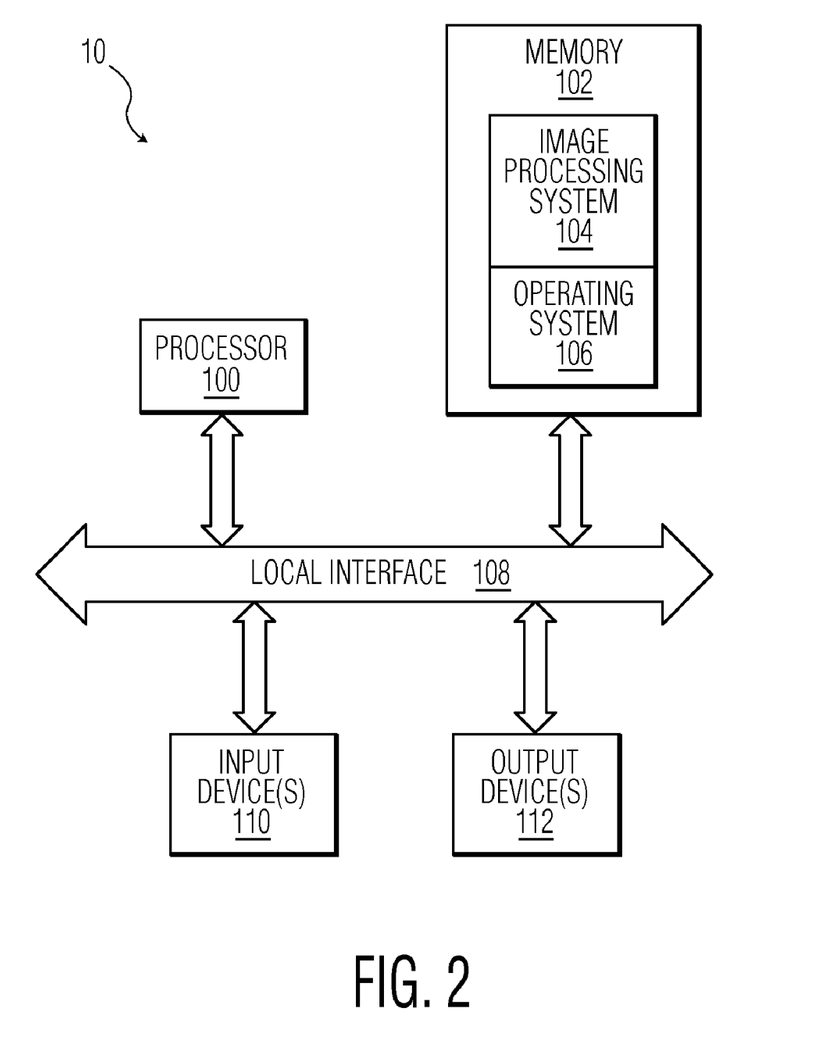
FIG. 2 is a functional block diagram of the system shown in FIG. 1.

FIG. 2 illustrates the functional components of the contrast imaging system 10 shown in FIG. 1. As depicted in FIG. 2, the system 10 typically comprises a processor 100, a memory 102, a local interface 108, and an output device 112. Typically, the memory 102 includes, inter alias, an image processing system 104, as well as an operating system 106. Furthermore, the memory 102 can include the memory 32 shown in FIG. 1. As will be appreciated by those having ordinary skill in the art, the image processing system 104 can be implemented in software, hardware, or a combination thereof within the image correction processor 30 shown in FIG. 1. It is to be noted that when implemented in software, the system 104 can be stored and transported on any computer readable medium for use by or in connection with an instruction execution system, apparatus, or device, such as a computer-based system, processor containing system, or other system that can fetch the instructions from the instruction execution system, apparatus, or device and execute the instructions.

In the context of this disclosure, a "computer readable medium" can be any means that can contain, store, communicate, propagate, or transport the program for use by or in connection with the instruction execution system, apparatus, or device. The computer readable medium can be, for example, an electronic, magnetic, optical, electromagnetic, infrared, or semiconductor system, apparatus, device, or propagation medium. More specific examples of computer readable media include the following: an electrical connection having one or more wires, computer diskette, random access memory (RAM), read only memory (ROM), erasable programmable read only memory (EPROM or Flash memory), an optical fiber, and a compact disk read only memory (CD ROM). It is to be noted that the computer readable medium can even be paper or another suitable medium upon which the program is printed as the program can be electronically captured, via for instance optical scanning of the paper or other medium, then compiled, interpreted, or otherwise processed in a suitable manner if necessary, and then stored in a computer memory.

Figure 3:
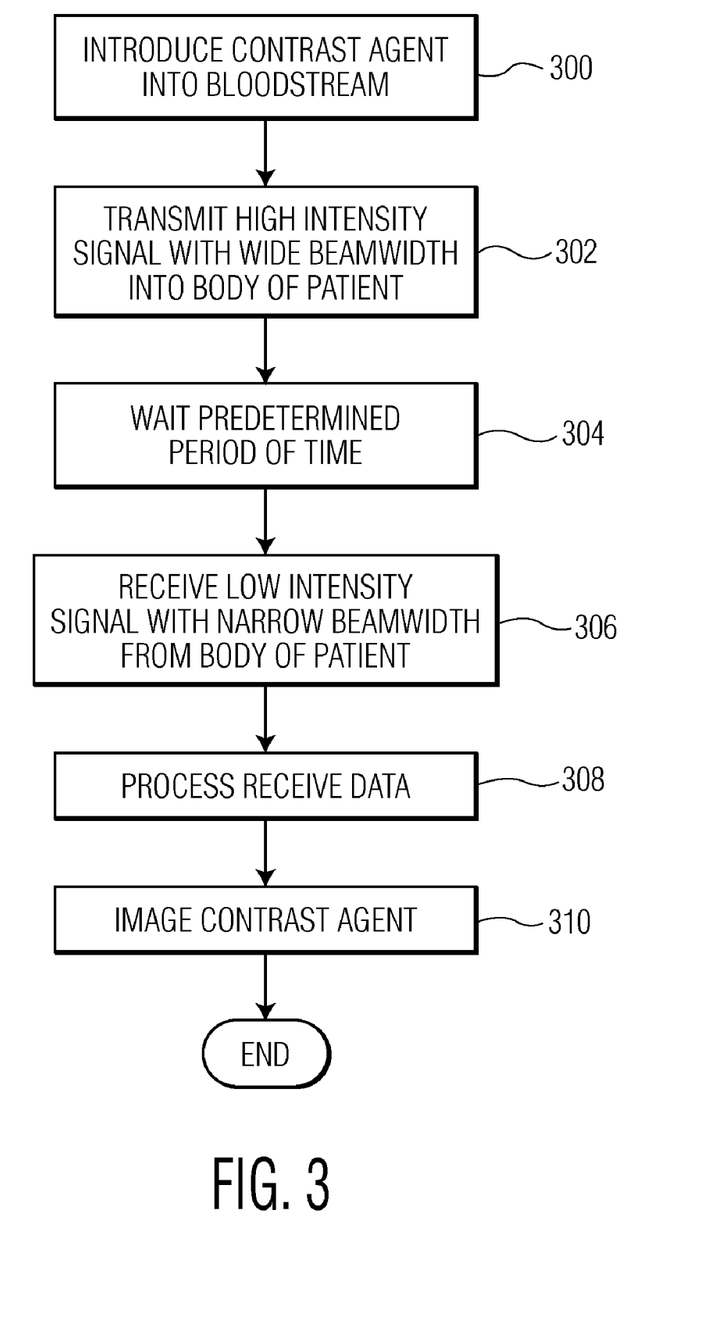
FIG. 3 is a flow diagram of a method for contrast imaging of the present invention.

With reference to FIG. 3, a contrast imaging method of the present invention will be discussed. In particular, FIG. 3 illustrates a high level contrast imaging method and therefore provides a general overview of the inventive method. As indicated in block 300, a contrast agent is first introduced intravenously into the patient's bloodstream. The contrast agent can comprise micro-bubbles of a heavy gas, such as a perfluorocarbon gas encapsulated in an outer shell made of protein, lipid, or other suitable material. Although the size of the agent may vary depending upon the application, these micro-bubbles normally are in the range of approximately 1.0 to 15 microns (µm) in diameter. As the contrast agent is introduced into the bloodstream, it travels through the right side of the heart and passes through the capillaries in the lungs. Next, the contrast agent (micro-bubbles) moves into the left side of the heart and as it passes out of the left side of the heart, it can also enter the coronary circulation of the heart. From the coronary circulation, the micro-bubbles can be delivered to the myocardium. Contrast imaging is used to image these bubbles, for example, in the myocardium and uses their presence or absence to detect ischemic regions in the myocardium, thereby predicting the viability of the myocardium in patients that are experiencing heart disease.

Figure 4:
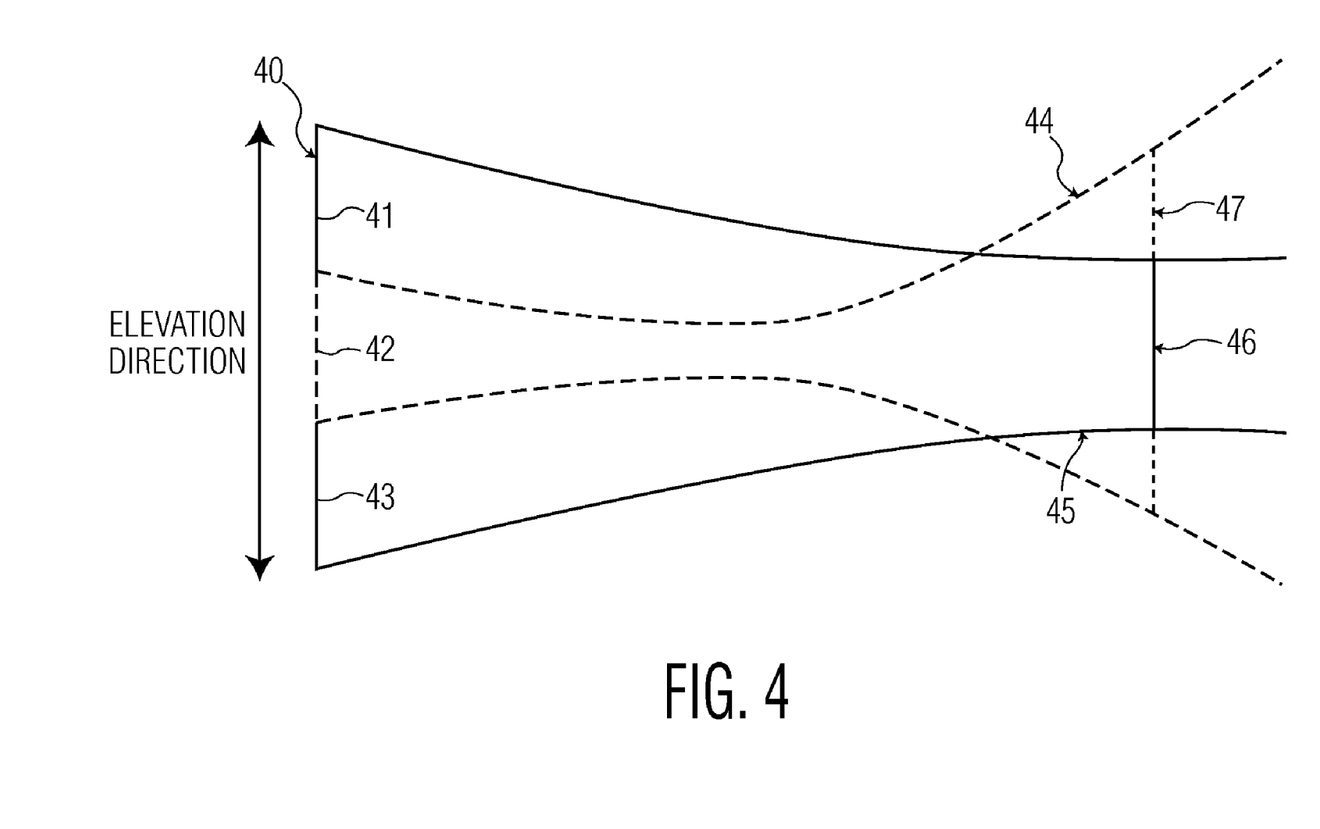
FIG. 4 is a schematic view of an ultrasound transducer for contrast imaging of the present invention.

As indicated in block 302, after the contrast agent has reached the image plane 46 and surrounding area 47 as shown in FIG. 4, ultrasound signals are transmitted into the body, and include both destructive frames and imaging frames. During destructive frames, the contrast agent, which is in a destruction plane in the body of the patient, is destroyed by focusing the ultrasound signals at a high enough acoustic pressure, which is in the range of current ultrasound systems, to disrupt the shell of the micro-bubbles and cause the gas which is encapsulated, to be dissolved into the bloodstream. The time for the dissolving of the gas into the blood stream differs based on the composition of the gas, but essentially the gas will re-absorb into the blood stream quite rapidly relative to the time involved in an ultrasound exam, and may be within the time to acquire a single frame of a real time ultrasound exam.

This means that if the narrower image plane where imaged either immediately or a very short period of time after a destruction frame, then the image would substantially comprise no contrast agent.

After a destruction frame, if a first image and second image are compared and signals in the first image disappear in the second image, then it is with a high probability that the signals represent the contrast agent. Otherwise, if signals are present in both of the images, then it is probably not related to the contrast agent, but rather an artifact.

The circulation of blood in the myocardium is fairly slow, such that if the contrast agent is destroyed during one or more destruction frames, replenishment of the myocardial region is typically for a normally functioning myocardial region on the order of four or five heart cycles, or about four or five seconds for an adult human. For an ischemic region where blood flow is reduced, replenishment can take significantly longer than in normal healthy tissue.

Therefore, a technique for detecting ischemic regions is by imaging with image frames at different triggering intervals. After one or more destruction frames, a pair of image frames can be taken with a small time delay which would allow time for the contrast agent to replenish. Next, the process can be repeated with the image frames taken with a slightly longer interval of time between the first and second image frames. In each repetition of the process, the time interval between first and second image frames is increased, which increases the amount of time for the contrast agent to replenish.

By viewing the intensity of the contrast agent in the image plane, a replenishment curve can be generated, which essentially is an exponentially increasing curve, and a region of this replenishment curve is related to the rate of blood flow in the myocardium. The rate of blood flow is a parameter of significant clinical interest because under certain conditions, it can indicate viability of the myocardium or the amount of ischemic damage to the region which is being imaged.

As indicated in block 304, a predetermined time after the destruction frame of the high intensity ultrasound beam, a low intensity imaging beam is transmitted during the imaging frame by the ultrasound transducer 12. As indicated in block 306, the low intensity beam, which is transmitted into the tissue of the patient, echoes from that tissue and is imaged via the ultrasound transducer 12 and 40, in the ultrasound imaging system 10.

It is advantageous to prevent the contrast agent, which is in the tissue surrounding the image plane, from moving into the image plane 46 due to movement of the tissue, for example, due to respiration of the heart and the lungs. To prevent the contrast agent from moving into the image plane 46 and creating image degradation, it is desirable to destroy the contrast agent in a destruction plane 47, which is thicker in the elevation direction 48 as shown in FIG. 4 than the image plane 46, which is being imaged. Both the image plane 46 and the destruction plane 47 are pie shaped sectors of a plane through the area of interest, for example, the heart. These planes have a thickness determined by the elevation focusing 44 and 45 of the ultrasound system 10, and vary with distance from the ultrasound transducer 12 and 40. The thickness of these planes 46 and 47 in the ultrasound transducer 12 and 40 is typically as thick as the face of the ultrasound transducer 12 and 40 at the surface of the ultrasound transducer 12 and 40. The thickness of the planes are thinned towards the elevation focus 44 and 45 and reaches a minimum, and then it diverges again and gets thicker at farther distances past the elevation focus 44 and 45. The divergence is not shown in FIG. 4.

By broadening the elevation focus in the elevation direction during the destruction frames by using, for instance, fewer sub-elements of the ultrasound transducer 41, 42 and 43, the contrast agent is destroyed in a wide area and substantially prevents the contrast agent from reentering the image plane 46 from motion during subsequent image frames. For a destructive frame or a series of destructive frames, using imaging of the heart as an example, it can be realized that only where energy is concentrated in the destruction plane is the contrast agent destroyed. Any contrast agent that lies outside of that plane is not destroyed. The destruction plane 47, which represents the wide area in which the contrast agent is destroyed during the destruction frames, is wider than the image plane 46 in which contrast agent is imaged during the imaging frames. By destroying a thicker slice of the contrast agent surrounding the image plane 46, the contrast agent in the surrounding tissue which moves into the image plane 46 due to motion of the patient or other internal movements within the body of the patient is not mistaken for reperfusion, thereby providing a more accurate measure of the rate of reperfused blood flow to or through the image plane 46. The destruction frames are typically only used for destroying the contrast agent and not for imaging.

As indicated in block 308, the received image echoed from the patient can be imaged using contrast data processing techniques, such as power inversion, etc. By destroying the micro-bubbles in the destruction plane and then contrast imaging over time the reperfusion of the micro-bubbles can be determined, which is representative of the amount of blood flow to or through the tissue which is being imaged. As indicated in block 310, the images can be provided on a video display, or other output device.

An embodiment of the present invention comprises an ultrasound transducer, which has the capability of elevation focusing in such a manner that during contrast imaging of the body of a patient, micro-bubbles of a contrast agent can be destroyed during a destructive frames in a region which includes the image plane as well as at least the surrounding tissue capable of moving into the image plane. The transducer is preferably a two-dimensional array transducer. By controlling the elevation focus of the ultrasound beam to be a thicker or less well focused ultrasound beam in the elevation direction, the contrast agent, which is both inside the image plane and adjacent to the image plane that could adversely effect the ultrasound image quality in the image plane through motion is intentionally destroyed. This provides the advantage that contrast imaging of the contrast agent reperfusion is improved over the conventional ultrasound imaging, because reperfusion of the tissues within the image plane occurs selectively and the ultrasound contrast imaging of the tissue within the image plane is substantially free from the effects of the contrast agent which can be carried into that region by motion or respiration. This means that the destruction thickness of the contrast agent during destruction frames is thicker than the image plane thickness.

In FIG. 4, a second technique, which can affect the elevation beamwidth focus, uses an ultrasound transducer 40 which has ultrasound transducer elements divided into three segments along the elevation direction. Other arrangements are possible, for example, a transducer with 5 sub-elements. By preferentially exciting only a number of those sub-elements, elevation focal changes can be controlled. For example, in an ultrasound transducer 40 which includes 3 sub-elements, by exciting the entire ultrasound transducer 40, which includes all sub-elements 41-43, a narrower focus is attainable in the elevation plane, and by exciting only the center sub-element 42 of the ultrasound transducer 40, a broader focus is attainable in the elevation plane. This is because, in a 3 sub-element ultrasound transducer 40, exciting the center sub-elements 42 only produces a small aperture with respect to the entire ultrasound transducer 40, which in turn produces a greater elevation focal thickness than with the entire ultrasound transducer 40. This allows for a thicker elevation focus 44 to provide improved contrast imaging of the reperfusion of a contrast agent by producing a destruction thickness 47 of the contrast agent during destruction frames which is thicker than the thickness of the image plane 46. This technique of utilizing the full elevation aperture of sub-elements or an array of transducer elements can be used during the imaging frames to produce a thinner elevation focus 45. During the destruction frames, the central portions of the aperture, in the elevation direction of the ultrasound transducer 40 can be used to produce a destruction plane 47, which is thicker than the image plane 46 thickness using all of the sub-elements. Although a 3-sub-element transducer is shown in FIG. 4, it is possible to produce substantially the same results with any number of sub-elements or an array of transducer elements.

A third technique, which affects the elevation focus, uses a two dimensional array of matrix elements which can be individually controlled for the ultrasound transducer 12. The array of matrix elements might be 64 elements by 64 elements for instance. It is advantageous to provide the two dimensional array with individual control of each of the matrix elements because controllability of the ultrasound beam is improved with respect to the segmented ultrasound transducer 40 which has a more limited number of sub-elements 41-43 and which does not have individual control over each of the sub-elements 41-43 of the ultrasound transducer 40. By adjusting the delay of each of the matrix array elements, elevation focus of an ultrasound beam of an ultrasound imaging system can be broadened and/or controlled.

Figure 5A:
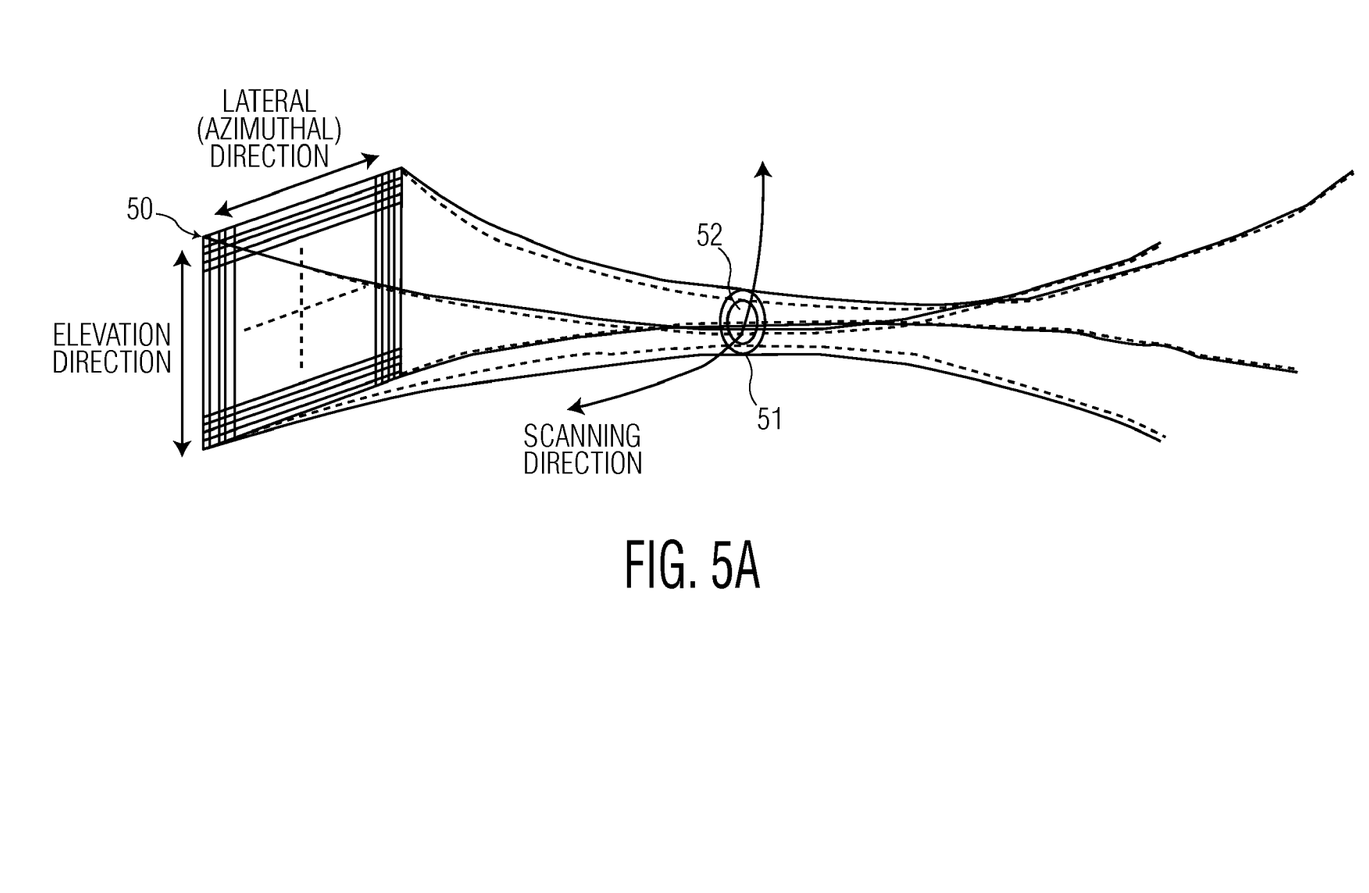
FIG. 5A is a plan view of a second embodiment of an ultrasound transducer for contrast imaging of the present invention.
Figure 5B:
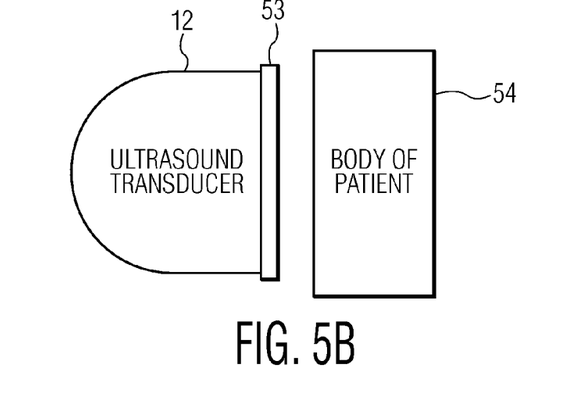
FIG. 5B is a schematic view of the second embodiment of the ultrasound transducer for contrast imaging of the present invention.

An ultrasound transducer 50 having an array of matrix array elements, which are individually controllable, is capable of steering and focusing a beam of ultrasound in a desired direction in the body and is capable of receiving, preferentially from desired directions in the body. The elevation focus can be electronically controlled during ultrasound imaging to change the elevation focus so that during the destruction frames the destruction region 51 of the contrast agent in the tissue of the patient is thicker than the imaging region 52 during the imaging frames. An acoustic coupler 53, shown in FIG. 5B, between the ultrasound transducer 12 and the body of the patient 54 can be provided and is preferably flat so as not to provide focal depth adjustment. The transducer elements are driven to produce an ultrasound signal, on transmit, and to receive an ultrasound signal, on receive. A central controller 22, as shown in FIG. 1, is used to control the time delay of the electrical signals, which drive the transducer matrix elements on transmit and which come from the transducer elements on receive. On receive, the electrical signals coming from respective transducer matrix elements, which can be time-delayed by the central controller 22, are summed at the summing point for imaging at the image plane. On transmit, an ultrasound beam is formed, which is in a preferential direction and has a focal depth in the body. The elevation focus is controlled on receive, by the respective matrix elements receiving the ultrasound echoes and the controller 22, providing respective delay times to electrical signals from each of the respective matrix elements. Those skilled in the art will appreciate that the operation is similar to phased array radar and antennas. The ultrasound imaging is done in real time and the transducers are an array of elements arranged in two dimensions, in a matrix array with a rectangular shape to each element. With no delay time between transducer elements in the ultrasound transducer, a ultrasound beam is produced which is perpendicular (in an azimuth direction) to the plane of transducer elements, by adjusting the time delay (phase) of the electrical signals to the transducer elements, the beam can be steered to desired angles relative to the plane of transducer elements and is represented in FIG. 5A by the scanning direction.

By controlling the timing of these elements in a linear delay profile across the plane of the matrix array, the beam can be controlled in the azimuth direction. It is desirable to focus the energy of the ultrasound signal as well as steer it. This can be accomplished by adding a spherical delay profile to the linear delay profile, which causes the energy to be focused at a certain range depth from the transducer. On transmit, the focal depth of the transmitted beam cannot be changed once the ultrasound signal is transmitted that therefore, it is advantageous to have a predetermined focal depth (in the elevation direction). On receive, since the ultrasound is received continuously from various depths as it propagates into the body and returns back to the transducer, it can be continuously updated to cause the focus to track with the depth of the returning ultrasound signals.

It is desirable to focus the ultrasound beam in both the azimuth direction and the elevation direction. This allows the steering of the beam within the body of a patient by controlling the beam in the azimuth direction and also focusing the energy of the beam at a specific depth in the elevation direction. By concentrating as much energy as possible in a small spot, spatial point resolution of small targets is possible.

During imaging frames, it is advantageous to provide a very narrow beam, which provides excellent spatial resolution. However, during destruction frames, contrary to a very narrow beam, the beam should advantageously be spatially uniform, which allows consistent destruction of the contrast agent throughout the field of view.

Figure 6:
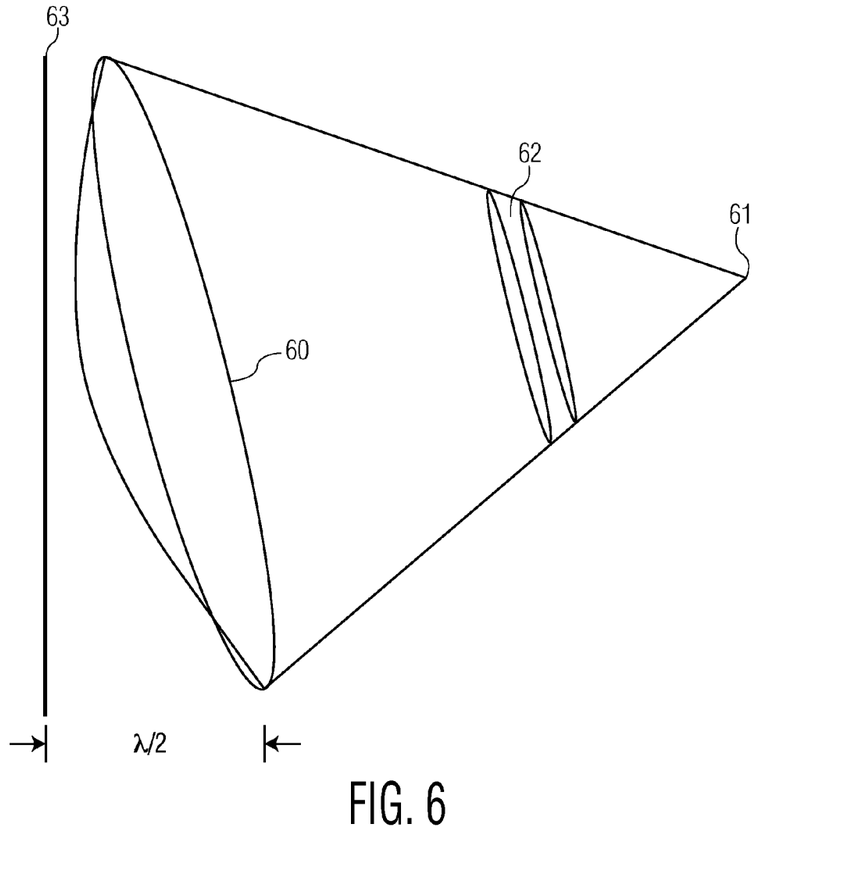
FIG. 6 is a schematic view of the operation of the second embodiment of an ultrasound transducer for contrast imaging of the present invention.

As shown in FIG. 6, elevation focus of the destruction frames can be controlled by applying different delays to the two-dimensional matrix array. Since the elements of a matrix array have different distances to the image plane, a spherical delay profile 60, as depicted in FIG. 5A, to the two-dimensional matrix array of the ultrasound transducer 50 allows, on transmit, for the transmission of a destruction frame which can be controllably focused in the elevation direction (depth into the patient's body), and it allows, on receive, for the reception of echoes which can be controllably received from different elevations in the patient's body. The spherical delay profile 60, which represents the phase delay in fractions of a wavelength of each pixel of a two-dimensional matrix array of the ultrasound transducer 50, is depicted as the distance from a reference plane 63. The maximum phase delay for any pixel of the two-dimensional matrix array is no more than $\lambda/2$. The spherical delay profile 60 represents different portions of a wavelength of sound for each matrix array element and to those skilled in the art, it represents a virtual parabolic array which can be focused in a desired direction with a desired focal depth.

Other techniques such as transmit frequency changes also allow for a broadened ultrasound beam. In particular, if the delay profile is fixed, for instance, by the physical geometry of the two-dimensional matrix array, the elevation focus can be changed by changing the frequency that excites the ultrasound transducer elements. Also an ultrasound beam affects a contrast agent more effectively at lower frequencies. Therefore, by lowering the frequency, which drives the ultrasound transducer 12 of the ultrasound system 10 during the destruction frames, the elevation focus can be changed and by controlling this change for successive destruction frames, the destruction plane 47 can be made thicker than the imaging plane 46.

Figure 7:
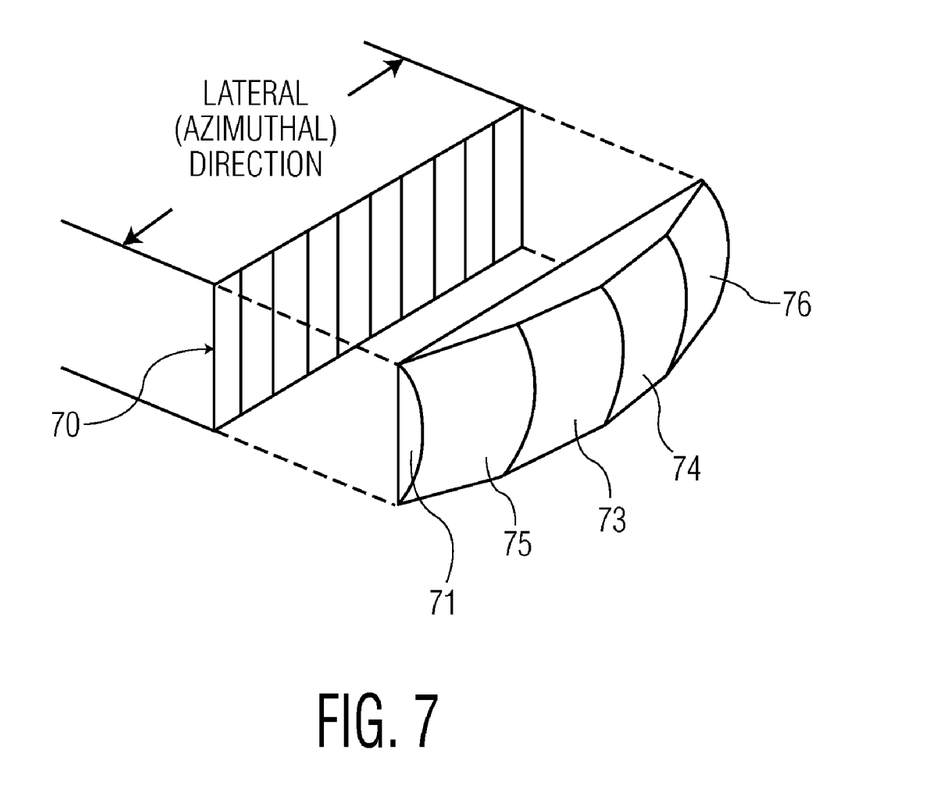
FIG. 7 is a plan view of a fourth embodiment of an ultrasound transducer for contrast imaging of the present invention.

A fourth technique to effect the elevation focus, disclosed in U.S. Pat. No. 5,738,098, uses an ultrasound transducer 70 with an elevation lens 71, as shown in FIG. 7, where the ultrasound transducer comprises a line of elements which are individually controllable and the elevation lens has a radius of curvature that varies in the azimuth direction (across the elements of the ultrasound transducer). The lens is composed of a material having a velocity of sound, which is slightly different from the velocity of sound in either the body of a patient or in the transducer elements. This has the same focusing effect on the ultrasound beam as an optical lens has on a light beam. This lens on a phased arrayed transducer is a cylindrical section, with the same depth across the phased array, except the depth varies from top to bottom. In particular, the lens increases in depth towards in the middle of the array of transducer elements and decreases at the top and bottom of the array of transducer elements. By selectively using either the central elements 73 and 74 or the widely spaced elements 75-76, the focal depth can be changed. By controlling this change in focal depth for successive destruction frames, the destruction plane can be made thicker than the image plane.

Figure 8:
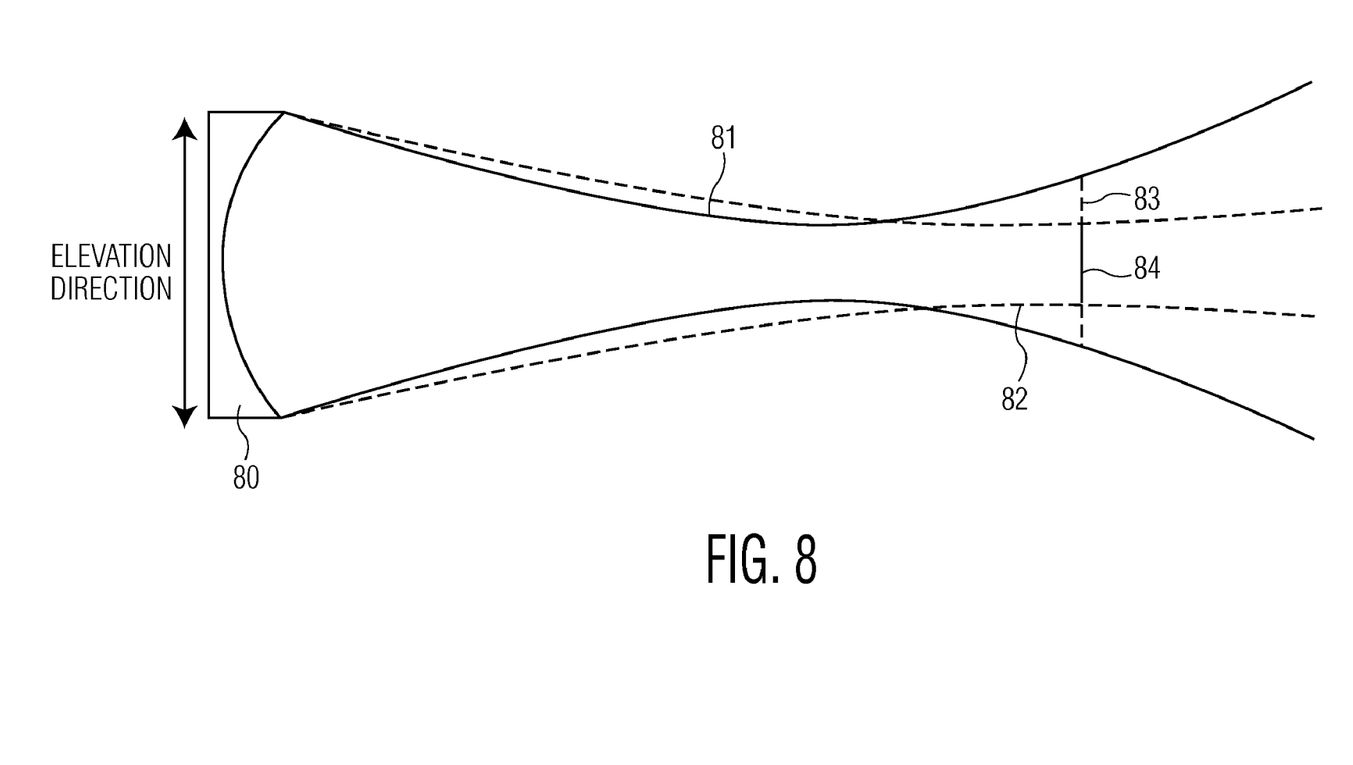
FIG. 8 is a schematic view of a fifth embodiment of an ultrasound transducer for contrast imaging of the present invention.

A fifth technique to effect the elevation focus uses an ultrasound transducer 80, as shown in FIG. 8, in which the surface of an array of transducer elements of the ultrasound transducer is curved in the elevation direction. By changing the frequency of excitation, the focal depth can be changed. By increasing the frequency of excitation, to a higher frequency a shallower elevation focus 81 can be achieved in comparison to a lower frequency of excitation, which produces a deeper elevation focus 82. By controlling this change in focal depth through changes in the frequency of excitation for successive destruction frames and image frames, the destruction plane 83 can be made thicker than the image plane 84.

These techniques, which provide a thick elevation focus during destruction frames to destroy a contrast agent in the image plane and directly adjacent areas and then provide a thinner elevation focus during imaging frames to image the reperfused contrast agent in the image plane, can be used in combination with most trigger imaging techniques, including those triggering synchronously to an ECG or respiration etc.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method for imaging a contrast agent within a body of a patient, comprising:
   transmitting high intensity ultrasound (HIFU) into a region of interest (ROI) within the patient in order signals to destroy the contrast agent in the ROI;
   waiting a predetermined time period after transmitting the HIFU signals;
   transmitting low intensity ultrasound (LIU) signals into the ROI; and
   receiving LIU signals echoed from the ROI in order to image only reperfused contrast agent in the ROI, wherein the receiving is from a narrower portion of the ROI exposed to the transmitting of the HIFU signals.

* * * * *